United States Patent
Gu et al.

[11] Patent Number: 5,971,942
[45] Date of Patent: Oct. 26, 1999

[54] INTESTINAL FLUID SAMPLER

[76] Inventors: Howard H. Gu, 1 Coleman St. #2A, West Haven, Conn. 06516; Hao Liang Gu, #9 Huangsi St. #416, Beijing, China

[21] Appl. No.: 08/759,815

[22] Filed: Dec. 3, 1996

[51] Int. Cl.⁶ ................................................. A61B 5/00
[52] U.S. Cl. ............................................................. 600/582
[58] Field of Search .................................. 600/582, 573, 600/577, 578

[56] References Cited

U.S. PATENT DOCUMENTS

| | | | |
|---|---|---|---|
| 3,315,660 | 4/1967 | Abella | 600/582 |
| 3,688,763 | 9/1972 | Cromarty | 600/582 |
| 4,046,149 | 9/1977 | Komiya | 606/127 |
| 4,417,583 | 11/1983 | Bechai | 128/662.06 |
| 4,632,110 | 12/1986 | Sanagi | 606/207 |
| 5,146,928 | 9/1992 | Esser | 128/756 |
| 5,327,897 | 7/1994 | Andresen | 600/582 |

*Primary Examiner*—Max Hindenburg
*Assistant Examiner*—Pamela Wingood

[57] ABSTRACT

A sampler is invented for collecting human or animal gastrointestinal fluid samples. The sampler is about the size of a medicine pill for oral administration. It has a hollow body 10, an opening 20, a seal 30, and a vacuum interior 40. When the sampler enters the gastrointestinal tract of a patient, the seal is dissolved or disabled and the surrounding fluid is sucked into the sampler by the vacuum inside. The sampler is then recovered from the patient's stool and the gastrointestinal fluid and substances within the sampler can be collected and analyzed.

3 Claims, 4 Drawing Sheets

2A

2B

2C

2D

2A

2B

2C

2D

3A

3B

INTESTINAL FLUID SAMPLER

BACKGROUND OF THE INVENTION (1) Field of the Invention

This invention relates to the techniques and equipment to sample fluids and substances from gastrointestinal (GI) tract for medical diagnosis and research.

(2) Description of the Prior Art

The composition of the GI fluids provides very useful information for doctors to diagnose patients for GI tract diseases. It indicates the physiological or pathological conditions of a patient, such as nutrient absorption, drug metabolism, microorganism distribution, and so on. Currently, samples of GI tract fluids are taken using mechanical devices, such as endoscopes. This type of devices are very expensive and inconvenient to use. They also cause pain and anxiety to patients, which may induce a significant change in the samples to be collected. Thus, GI tract fluids are not routinely sampled which has significantly limited doctors' accessibility to important information.

Simpler, more convenient and less expensive devices for GI tract fluid sampling are long awaited. The current invention meets this demand. It is totally different from the prior art in design and method.

SUMMARY

A new device is invented for sampling GI tract fluids and substances. The sampler is made of a hollow object which is about the size of a medicine pill for oral administration. The hollow sampler has a vacuum interior and an opening which is blocked by a seal. When the sampler enters the GI tract of a patient, the seal is dissolved or disabled and the surrounding fluid is sucked into the sampler by the vacuum inside. The sampler is then recovered from the patient's stool and the fluid and substances within the sampler can be collected and analyzed.

OBJECTS AND ADVANTAGES

The objects and advantages of the present invention are to provide a device for sampling GI tract fluids (1) with a simpler procedure;
(2) which is very easy to use;
(3) which does not cause pain and anxiety for patients;
(4) which is less expensive;
(5) which can be performed by patients at home.

REFERENCE NUMERALS IN DRAWINGS

10 hollow body
20 opening
30 seal
40 vacuum interior

DESCRIPTION OF THE EMBODIMENT

Figure 1:
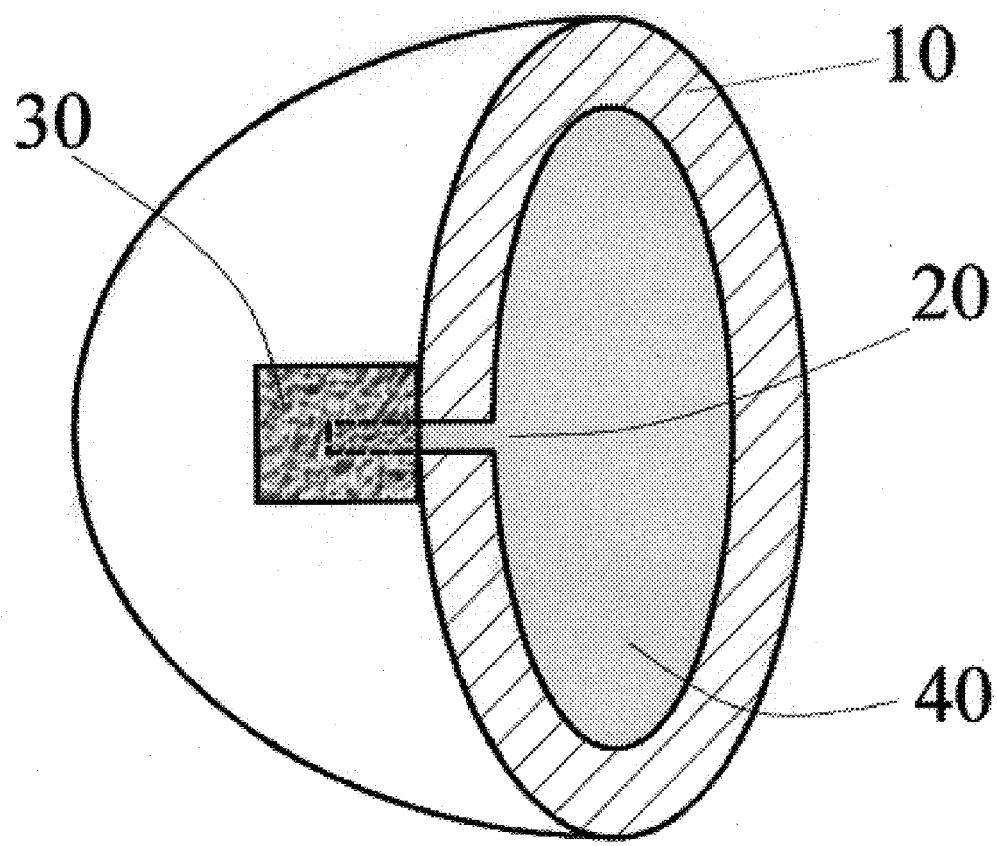
FIG. 1 shows an example of the embodiments of the GI tract fluid sampler.
Figure 2:
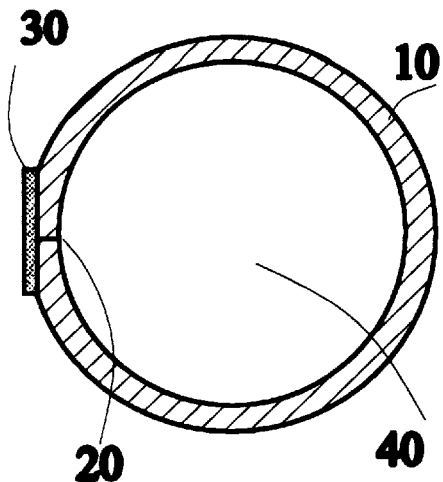
FIGS. 2A to 2D illustrate a mechanism of an opening being opened and closed in the presence and absence of internal vacuum.
Figure 2:
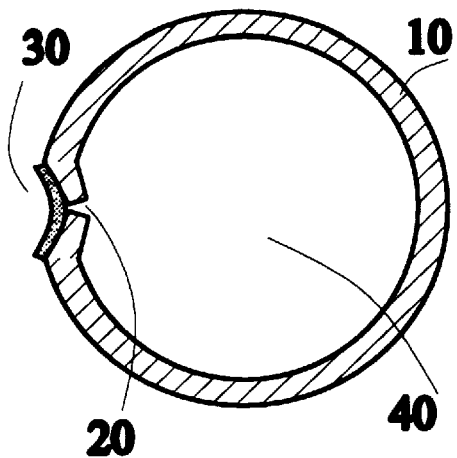
Figure 2:
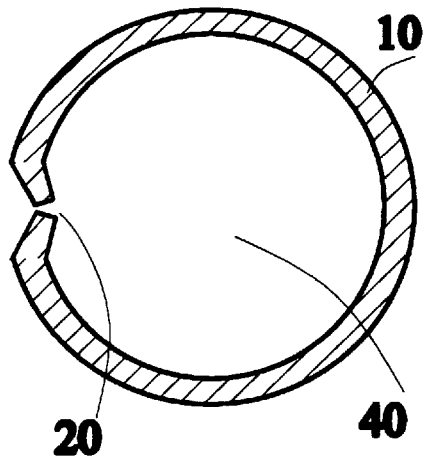
Figure 2:
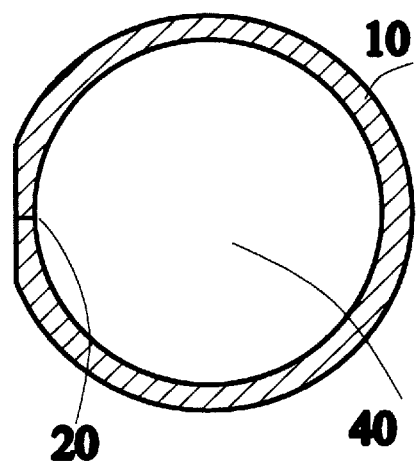
Figure 3:
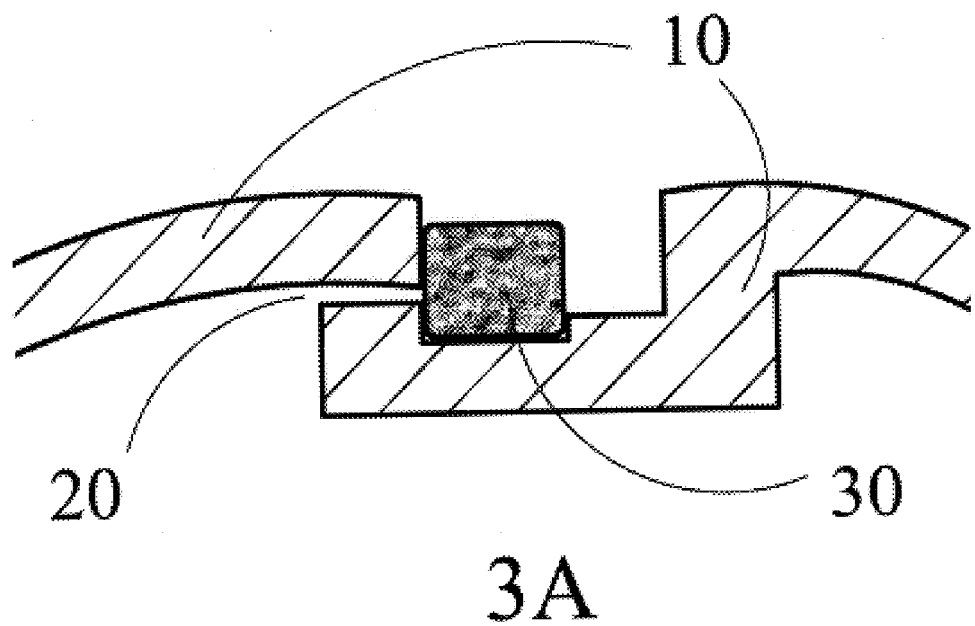
FIGS. 3A to 3B show one example of the means for disabling the seal.
Figure 3:
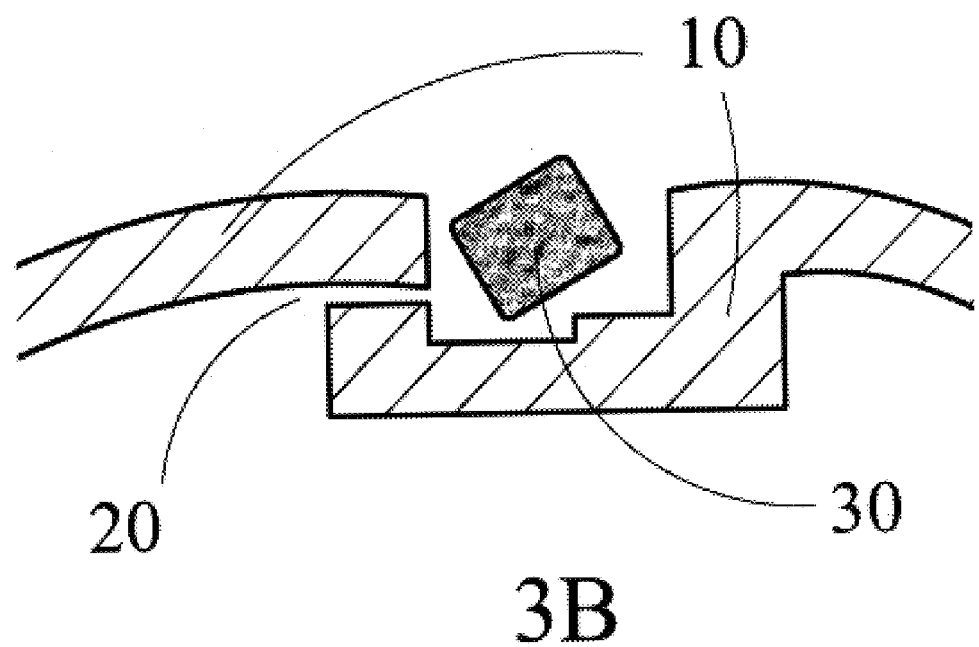

FIGS. 1 to 3

An example of the embodiments of the present invention is illustrated in FIG. 1. The figure shows a sampler being cut in half. It comprises a hollow body 10, an opening 20, a seal 30, and a vacuum interior 40. Hollow body 10 is made of an inert material, such as polypropylene, which does not cause irritation. It has a shape of a ball (an oval, a disk, or a cylinder) with a diameter of about 10 millimeter (mm) and a thickness of 1–2 mm. Opening 20 is a gap of 1–5 mm long and 0.1–0.5 mm wide which allows fluid to pass through when driven by a vacuum but little fluid exchange when equal pressure is reached on both sides. Seal 30 is a seal patch made of a material, such as cellulose acetate phthalate, glyceryl stearates, paraffin, or epoxy compounds, which will disintegrate or be dissolved in the GI tract fluid. Epoxy compounds with increasing concentration of chloramphenicol have a decreased dissolution rate. Seal patches of various thickness or property dissolves at different time allowing the collection of samples from different sections of the GI tract. Vacuum interior 40 provides driving force to suck fluid into the sampler.

FIGS. 2A to 2D are cross sections of the sampler showing a mechanism of an opening being opened and closed in the presence and absence of an internal vacuum. FIG. 2A shows a sampler without internal vacuum with the opening in its original shape of a closed state. FIG. 2B shows a sampler with an internal vacuum which forces the edges of the opening to bend inward and thus to open a gap. FIG. 2C shows that the seal is dissolved and fluid being sucked into the vacuum interior. FIG. 2D shows that after the fluid has filled up the vacuum space, the opening springs back to its original shape of the closed state.

FIGS. 3A and 3B show one example of other means for disabling the seal than dissolving it. Seal 30 is a plug made of magnetic material coated with inert plastic. FIG. 3A shows that the plug (seal 30) blocks opening 20. FIG. 3B shows that the removal of the plug disables the seal and allows fluid to be sucked into the vacuum interior through the opening. The magnetic plug seal can be removed remotely with a magnetic field instead of dissolution or direct mechanical means.

Figure 4:
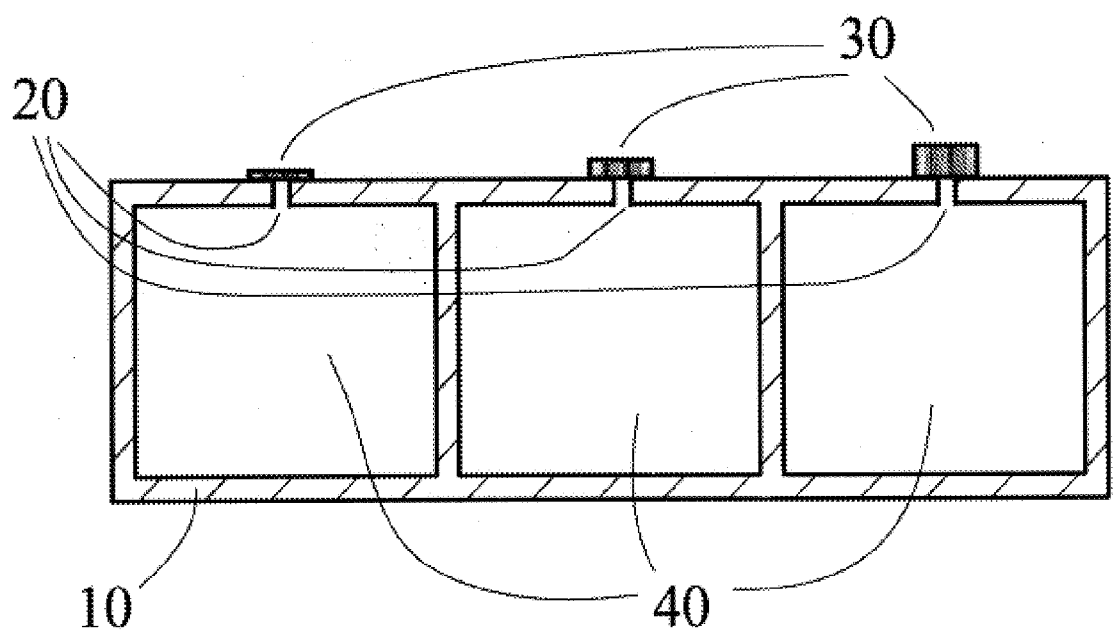
FIG. 4 shows the cross section of a cylinder-shaped sampler with multiple chambers.

FIG. 4 shows an example of a sampler with multiple chambers. The figure shows a cross section view along the axis of a cylinder shaped sampler with three chambers. Seal 30 are seal patches made of materials that dissolves in GI tract fluid. It is illustrated in the figure that the seal patches have different thickness so that they dissolve completely at different time, and therefore, fluids from different sections of GI tract can be collected.

Operation

The sampler is orally administered by a patient and later collected from the stool of the patient. The seal is dissolved in the patient's GI tract and surrounding fluid is sucked into the sampler. Several sampler with different seal properties can be administered by a patient so that fluid samples from different sections of GI tract can be collected. A sampler with multiple chambers (FIG. 4) will accomplish the same goal. Alternatively, the position of the sampler (with the design shown in FIG. 3) can be monitored with ultrasound or other means, and when the sampler reaches a desired section of the GI tract, the magnetic plug is removed with a strong magnetic field and a sample is collected in that specific section of GI tract.

Conclusion, Ramifications, and Scope

The current methods used to collect samples from the GI tract of a patient requires the use of mechanical devices. This type of devices are very expensive, inconvenient, and usually cause anxiety and pain which may induce a significant change in the samples to be collected. The new sampler would solve these problems and provides doctors with important information to diagnose their patients. When information of GI tract is easily available, novel diagnostic methods could be developed for GI tract diseases including cancers. The sampler is also a good tool for research in drug metabolism, nutrient absorption, microorganism distribution and other physiological and biochemical processes. The sampler also can be used for animals.

While my above description contains many specificities, these should not be construed as limitations on the scope of the invention, but rather as exemplifications of preferred embodiments thereof. Many other variations are possible. Accordingly, the scope of the invention should be determined not by the embodiment illustrated, but by the appended claims and their legal equivalents.

I claim:

1. A device for sampling gastrointestinal fluid and substances, comprising:

(a) a hollow body with multiple chambers, (b) a vacuum interior within each said chamber, (c) at least one opening on each said chamber, and (d) dissolvable sealing patches with various thickness blocking said openings, whereby they will be dissolved at different time and therefore fluid samples from different sections of the gastrointestinal tract can be collected into different chambers.

2. A device for sampling gastrointestinal fluid and substances, comprising:

(a) a hollow body with multiple chambers, (b) a vacuum interior within each said chamber, (c) at least one opening on each said chamber, and (d) dissolvable sealing patches with various properties blocking said openings, whereby they will be dissolved at different time and therefore fluid samples from different sections of the gastrointestinal tract can be collected into different chambers.

3. A method for sampling gastrointestinal fluid and substances using the device of any of claims 1 or 2 where said device is orally administered by a person or an animal and recovered from the stool, and the fluid and substances collected within said device can be analyzed.

* * * * *